US011180576B2

(12) United States Patent
Choi et al.

(10) Patent No.: US 11,180,576 B2
(45) Date of Patent: Nov. 23, 2021

(54) COMBINATION OF CROSS-LINKED HYALURONIC ACIDS AND METHOD OF PREPARING THE SAME

(71) Applicant: HANMI PHARM. CO., LTD., Hwaseong-si (KR)

(72) Inventors: Sung Chul Choi, Suwon-si (KR); Hyun Il Kim, Paju-si (KR); Ki Young Yang, Cheonan-si (KR); Hyo Seung Park, Pyeongtaek-si (KR); Back Ho Lee, Pyeongtaek-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 16/448,180

(22) Filed: Jun. 21, 2019

(65) Prior Publication Data

US 2019/0315887 A1    Oct. 17, 2019

Related U.S. Application Data

(63) Continuation of application No. 15/322,326, filed as application No. PCT/KR2016/005819 on Jun. 1, 2016, now abandoned.

(30) Foreign Application Priority Data

Jan. 29, 2016  (KR) .................. 10-2016-0011843
Feb. 1, 2016   (KR) .................. 10-2016-0012519

(51) Int. Cl.
| | | |
|---|---|---|
| C08B 37/08 | (2006.01) |
| A61K 47/02 | (2006.01) |
| A61L 27/20 | (2006.01) |
| A61K 9/00 | (2006.01) |
| A61K 47/08 | (2006.01) |
| A61K 47/10 | (2017.01) |
| A61K 9/06 | (2006.01) |
| A61K 8/02 | (2006.01) |
| A61Q 19/08 | (2006.01) |
| C08L 5/08 | (2006.01) |
| A61K 8/73 | (2006.01) |
| A61K 47/36 | (2006.01) |
| C08J 3/24 | (2006.01) |

(52) U.S. Cl.
CPC ........ *C08B 37/0072* (2013.01); *A61K 8/0241* (2013.01); *A61K 8/735* (2013.01); *A61K 9/0024* (2013.01); *A61K 9/06* (2013.01); *A61K 47/02* (2013.01); *A61K 47/08* (2013.01); *A61K 47/10* (2013.01); *A61K 47/36* (2013.01); *A61L 27/20* (2013.01); *A61Q 19/08* (2013.01); *C08J 3/24* (2013.01); *C08L 5/08* (2013.01); *A61L 2400/06* (2013.01); *A61L 2430/34* (2013.01); *C08J 2305/08* (2013.01); *C08L 2205/025* (2013.01)

(58) Field of Classification Search
CPC .. C08B 37/0072; A61K 31/728; A61K 31/738
See application file for complete search history.

(56) References Cited

U.S. PATENT DOCUMENTS

| | | | | | |
|---|---|---|---|---|---|
| 4,713,448 | A | * | 12/1987 | Balazs | A61P 7/02 536/55.1 |
| 5,143,724 | A | * | 9/1992 | Leshchiner | A61K 9/0019 424/422 |
| 2006/0105022 | A1 | | 5/2006 | Yokokawa et al. | |
| 2006/0148755 | A1 | * | 7/2006 | Bailleul | A61P 5/44 514/54 |
| 2009/0163441 | A1 | | 6/2009 | Gobbo et al. | |
| 2012/0258155 | A1 | | 10/2012 | Wenk et al. | |

FOREIGN PATENT DOCUMENTS

| | | |
|---|---|---|
| JP | 2009-536625 A | 10/2009 |
| JP | 2011-506719 A | 3/2011 |
| WO | 2006/051950 A1 | 5/2006 |
| WO | 2014/206500 A1 | 12/2014 |

OTHER PUBLICATIONS

Gigante, A. et al "The role of intra-articular hyaluronan . . . " Rheumatol. Int., vol. 31, pp. 427-444. (Year: 2011).*
Yui, N. et al "Inflammation responsive degradation of crosslinked hyaluronic . . . " J. Controlled Release, vol. 22, pp. 105-116. (Year: 1992).*
Santoro et al., "Rheological properties of cross-linked hyaluronic acid dermal fillers", J. Appl. Biomater. Biomech., 2011, vol. 9, No. 2, pp. 127-136.
Japanese Office Action dated Mar. 3, 2020 of Japanese Patent Application No. 2018-538690, five pages.

* cited by examiner

*Primary Examiner* — Leigh C Maier
(74) *Attorney, Agent, or Firm* — Vorys, Sater, Seymour & Pease LLP; Mih Suhn Koh

(57) ABSTRACT

Provided are a combination of cross-linked hyaluronic acids comprising: a cross-linked hyaluronic acid having an elasticity of about 50 to about 200 Pa and a viscosity of about 20 to about 100 Pa, and a cross-linked hyaluronic acid having an elasticity of about 400 to about 800 Pa and a viscosity of about 40 to about 100 Pa, and a method for preparing the same.

7 Claims, 3 Drawing Sheets

COMBINATION OF CROSS-LINKED HYALURONIC ACIDS AND METHOD OF PREPARING THE SAME

CROSS-REFERENCE TO RELATED APPLICATION

This application is a Continuation Application of U.S. patent application Ser. No. 15/322,326, filed Dec. 27, 2016, which was a National Phase Application filed under 35 U.S.C. 371 as a national stage of PCT/KR2016/005819, filed Jun. 1, 2016, and claims the benefit of Korean Patent Application No. 10-2016-0011843, filed on Jan. 29, 2016, and Korean Patent Application No. 10-2016-0012519, filed on Feb. 1, 2016, in the Korean Intellectual Property Office, the disclosures of which are incorporated herein in their entireties by reference.

TECHNICAL FIELD

The present disclosure relates to a preparation method of a cross-linked hyaluronic acid and a combination of cross-linked hyaluronic acids having a viscoelasticity appropriate for use in the living body, comprising the cross-linked hyaluronic acid prepared using the same method.

BACKGROUND ART

Hyaluronic acids are a biopolymer material including linearly linked repeating units consisting of N-acetyl-D-glucosamine and D-glucuronic acid, and are also known to be prevalent in animal placenta, vitreous humour, synovial fluid, rooster combs, and the like. Hyaluronic acids are also known to be produced via fermentation by microorganisms of the *Streptococcus* spp. (for example, *Streptococcus equi*, or *Streptococcus zooepidemicus*) or the *Staphylococcus* spp.

Synvisc-One®, a cross-linked hyaluronic acid injection, which provide its effect lasting up to 6 months with one injection, are commercially available in the U.S. Synvisc-One® includes a cross-linked hyaluronic acid obtained by extracting hyaluronic acids from rooster combs with a formalin-containing aqueous solution, having a low viscoelasticity due to the light cross-linking of proteins connected to hyaluronic acids with formalin (U.S. Pat. No. 4,713,448). The lightly cross-linked hyaluronic acid is combined with its further cross-linked hyaluronic acid having increased viscoelasticity prepared by further cross-linking the lightly cross-linked hyaluronic acid using divinyl sulfone (DVS) as a cross-linking agent, thereby preparing a combination of cross-linked hyaluronic acids (Synvisc-One®) having appropriate viscoelasticity for applying to the joint cavity in the human body.

However, hyaluronic acids of animal origin such as from rooster combs may have a quality control problem due to animal-origin viruses and inconsistent quality of source material.

DETAILED DESCRIPTION OF THE INVENTION

Technical Problem

The present disclosure provides a method of preparing a cross-linked hyaluronic acid having a low viscoelasticity.

The present disclosure provides a combination of cross-linked hyaluronic acids having an appropriate viscoelasticity applicable to the human body.

The present disclosure provides a biocompatible material including the combination of cross-linked hyaluronic acids.

The present disclosure provides a method of preparing the combination of cross-linked hyaluronic acids having an appropriate viscoelasticity applicable to the living body.

Technical Solution

According to an aspect of the present disclosure, there is provided a method of preparing a cross-linked hyaluronic acid having an elasticity of about 50 Pa to about 200 Pa and a viscosity of about 20 Pa to about 100 Pa, the method including cross-linking hyaluronic acid with an epoxy-based cross-linking agent having at least two epoxy functional groups in an ethanol-containing aqueous alkaline solution.

According to another aspect of the present disclosure, there is provided a method of preparing a cross-linked hyaluronic acid having an elasticity of about 400 Pa to about 800 Pa and a viscosity of about 40 Pa to about 100 Pa, the method including further cross-linking the cross-linked hyaluronic acid prepared using the above-described method with an epoxy-based cross-linking agent having at least two epoxy functional groups in an aqueous alkaline solution.

According to another aspect of the present disclosure, there is provided a combination of cross-linked hyaluronic acids, the combination including a cross-linked hyaluronic acid having an elasticity of about 50 to about 200 Pa and a viscosity of about 20 to about 100 Pa, and a cross-linked hyaluronic acid having an elasticity of about 400 to about 800 Pa and a viscosity of about 40 to about 100 Pa.

According to another aspect of the present disclosure, there is provided a combination of cross-linked hyaluronic acids, the combination including: a cross-linked hyaluronic acid having an elasticity of about 50 to about 200 Pa and a viscosity of about 20 to about 100 Pa prepared using a method including cross-linking hyaluronic acid with an epoxy-based cross-linking agent having at least two epoxy functional groups in an ethanol-containing aqueous alkaline solution; and a cross-linked hyaluronic acid having an elasticity of about 400 to about 800 Pa and a viscosity of about 40 to about 100 Pa prepared using a method including cross-linking the cross-linked hyaluronic acid having an elasticity of about 50 to about 200 Pa and a viscosity of about 20 to about 100 Pa with an epoxy-based cross-linking agent having at least two epoxy functional groups in an aqueous alkaline solution.

According to another aspect of the present disclosure, there is provided a biocompatible material including any of the above-described combinations of cross-linked hyaluronic acids.

According to another aspect of the present disclosure, there is provided a method of preparing a combination of cross-linked hyaluronic acids, the method including combining the cross-linked hyaluronic acid having an elasticity of about 50 to about 200 Pa and a viscosity of about 20 to about 100 Pa with the cross-linked hyaluronic acid having an elasticity of about 400 to about 800 Pa and a viscosity of about 40 to about 100 Pa, wherein the combining ratio is adjusted to meet a target viscoelasticity of the combination of cross-linked hyaluronic acids to be prepared.

Advantageous Effects

According to the one or more embodiments of the present disclosure, in a method of preparing a cross-linked hyaluronic acid using an epoxy-based cross-linking agent in an aqueous alkaline solution, ethanol is added to the aqueous alkaline solution, so that the prepared cross-linked hyaluronic acid may have a low viscoelasticity. The viscoelasticity of the cross-linked hyaluronic acid may be adjusted depending on the reaction conditions. A combination of cross-linked hyaluronic acids having a desired viscoelasticity may be prepared by combining the cross-linked hyaluronic acid having a low viscoelasticity with the cross-linked hyaluronic acid having a high viscoelasticity obtained through further cross-linking of the low-viscoelasticity cross-linked hyaluronic acid. Therefore, a biocompatible combination of cross-linked hyaluronic acids having a viscoelasticity appropriate for use in the human body, and in particular, having a similar viscoelasticity similar to the human synovial fluid may be prepared for effective use in osteoarthritis treatment.

MODE FOR INVENTION

Figure 1:
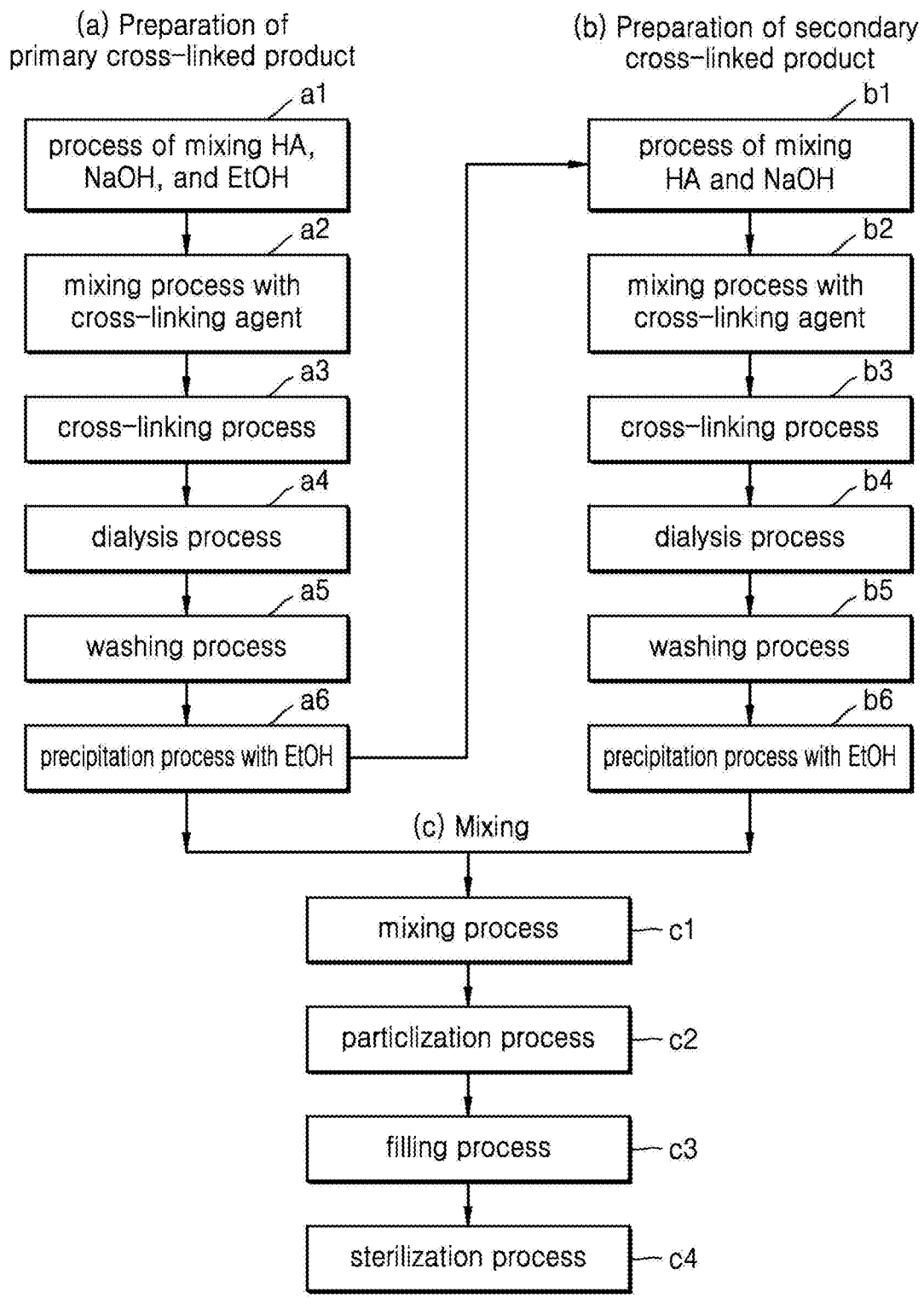
FIG. 1 is a flowchart illustrating a method of preparing a combination of cross-linked hyaluronic acids, according to an embodiment of the present disclosure.

Unless otherwise defined, all terms (including technical and scientific terms) used herein have the same meaning as commonly understood by one of ordinary skill in the art to which this invention belongs. Although exemplary methods or materials are listed herein, other similar or equivalent ones are also within the scope of the present invention. Any numerical expression herein may be construed as the meaning of approximation, such as "about", unless otherwise defined. All publications disclosed as references herein are incorporated in their entirety by reference.

The inventors of the present disclosure attempted to prepare lightly cross-linked hyaluronic acids from purified source material of hyaluronic acids originating from microorganisms, but failed due to low protein content of the purified hyaluronic acids of microorganism origin. As a result of research into a method of light cross-linking of purified hyaluronic acids of microorganism origin having low protein content, the inventors found that lightly cross-linked hyaluronic acids having a novel range of low viscoelasticity are obtained by introducing ethanol to an aqueous alkaline solution where a conventional hyaluronic acid cross-linking reaction with a multifunctional epoxy-based cross-linking agent takes place. The inventors also found that cross-linked hyaluronic acids having an increased viscoelasticity may be obtained by a secondary cross-linking reaction of the lightly cross-linked hyaluronic acids having a low viscoelasticity with a multifunctional epoxy-based cross-linking agent.

An aspect of the present disclosure provides a cross-linked hyaluronic acid having an elasticity of 50 to 200 Pa and a viscosity of 20 to 100 Pa.

The cross-linked hyaluronic acids are not limited only to those cross-linked hyaluronic acids obtained by a specific cross-linking method.

In some embodiments, the cross-linked hyaluronic acid may be prepared by a method including a step of cross-linking hyaluronic acids with an epoxy-based cross-linking agent having at least two epoxy functional groups in an ethanol-containing aqueous alkaline solution. This will be described later in more detail.

The cross-linked hyaluronic acid having an elasticity of 50 to 200 Pa and a viscosity of 20 to 100 Pa may be used as any biocompatible material using hyaluronic acids, for example, selected from the group consisting of arthritis treatment implants, wrinkle fillers, cosmetic fillers, and drug carriers. The cross-linked hyaluronic acid may be used as a more appropriate biocompatible material in a combination with a cross-linked hyaluronic acid having an increased viscoelasticity that may be prepared via a further cross-linking reaction, if required.

Another aspect of the present disclosure provides a method of preparing a cross-linked hyaluronic acid having an elasticity of 50 to 200 Pa and a viscosity of 20 to 100 Pa, the method including cross-linking hyaluronic acids with an epoxy-based cross-linking agent having at least two epoxy functional groups in an ethanol-containing aqueous alkaline.

Another aspect of the present disclosure provides a method of preparing a cross-linked hyaluronic acid having an elasticity of 400 to 800 Pa and a viscosity of 40 to 100 Pa, the method including further cross-linking the cross-linked hyaluronic acid prepared using the above-described method with an epoxy-based cross-linking agent having at least two epoxy functional groups in an aqueous alkaline solution.

As used herein, the cross-linked hyaluronic acid having an elasticity of 50 to 200 Pa and a viscosity of 20 to 100 Pa, prepared using the above-describe method, is also referred to as a "primary cross-linked product", and the cross-linked hyaluronic acid having an elasticity of 400 to 800 Pa and a viscosity of 40 to 100 Pa, prepared by further cross-linking the primary cross-linked product, is also referred to as a "secondary cross-linked product." The primary cross-linked product may be in the form of hyaluronic acid gel, and the secondary cross-linked product may be in the form of hyaluronic acid particles.

As used herein, the term "hyaluronic acid" may be construed as any of hyaluronic acid, a salt of hyaluronic acid, or any mixtures thereof. The salt of hyaluronic acid may be any biocompatible salt form, for example, selected from the group consisting of sodium hyaluronate, potassium hyaluronate, magnesium hyaluronate, zinc hyaluronate, cobalt hyaluronate, tetrabutylammonium hyaluronate, and any combinations thereof. In some embodiments, the salt of hyaluronic acid may be sodium hyaluronate.

The hyaluronic acid may have a molecular weight of about 100,000 to about 6,000,000. A viscoelasticity of the cross-linked hyaluronic acid may vary depending on the molecular weight of the hyaluronic acid.

In some embodiments, the hyaluronic acid may be sodium hyaluronate having a molecular weight of about 100,000 to about 6,000,000.

The hyaluronic acid may include any hyaluronic acids known in the art to which the present disclosure pertains. The hyaluronic acid may be obtained from any sources. The hyaluronic acid may be obtained, for examples, from animal sources (for example, animal placenta, rooster combs, or the like) or any microorganisms that may produce hyaluronic acids through fermentation (for example, microorganisms of the *Staphylococcus* spp., the *Streptococcus* spp., or the like).

In some embodiments, the hyaluronic acid may be hyaluronic acid of microorganism origin, for example, of the *Staphylococcus* spp. microorganism origin. Hyaluronic acids of microorganism origin may be free of the problems with animal-origin hyaluronic acids, such as virus or inconsistent quality of source material, and thus may be advantageous in view of quality control in drug preparation.

The epoxy-based cross-linking agent having at least two epoxy functional groups may be any epoxy-based cross-linking agent having at least two epoxy functional groups known in the art, for example, selected from the group consisting of 1,4-butanediol diglycidyl ether (BDDE), ethylene glycol diglycidyl ether (EGDGE), 1,6-hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, trimethylpropane polyglycidyl ether, 1,2-(bis(2,3-epoxypropoxy)ethylene, pentaerythritol polyglycidyl ether, sorbitol polyglycidyl ether, and any combinations thereof.

In some embodiments, the epoxy-based cross-linking agent having at least two epoxy functional groups may be BDDE, EGDGE, 1,6-hexanediol diglycidyl ether, or any combinations thereof.

In some embodiments, the amount of the epoxy-based cross-linking agent that may be reacted with the hyaluronic acid or cross-linked hyaluronic acid may be in a range of about 10 μl/g to about 100 μl/g, and in some embodiments, about 20 μl/g to about 100 μl/g with respect to the hyaluronic acid or cross-linked hyaluronic acid. When the amount of the epoxy-based cross-linking agent that reacted with the hyaluronic acid or cross-linked hyaluronic acid is less than these ranges, gel formation may not occur in preparation of the primary cross-linked product or cross-linked particles may not be obtained in preparation of the secondary cross-linked product. When the amount of the epoxy-based cross-linking agent that reacted with the hyaluronic acid or cross-linked hyaluronic acid is more than these ranges, a primary cross-linked product may be obtained in the form of particles, not an intended gel having a low viscoelasticity.

The ethanol-containing aqueous alkaline solution may be an aqueous alkaline solution containing about 5 to 13% w/w of ethanol. The viscosity of the cross-linked hyaluronic acid may be controlled with the concentration of the ethanol. When the concentration of the ethanol is within this range, sodium hyaluronate may be stably mixed with the ethanol, not extracted by the ethanol, so that a cross-linking reaction may take place.

The aqueous alkaline solution may be an aqueous alkaline solution of about pH 9 to 13. The aqueous alkaline solution may be any aqueous alkaline solution known to be available in preparation of cross-linked hyaluronic acids. For example, the aqueous alkaline solution may be an aqueous sodium hydroxide solution, an aqueous potassium hydroxide solution, or ammonia water. For example, the aqueous alkaline solution may be an aqueous sodium hydroxide solution.

In some embodiments, the ethanol-containing aqueous alkaline solution may be an about 0.7 to about 1.3% w/w aqueous sodium hydroxide solution containing about 5 to about 13% w/w of ethanol.

As a result of the experiment, hyaluronic acid gel was formed only when hyaluronic acids reacted with an epoxy-based cross-linking agent having at least two epoxy functional groups in an aqueous alkaline solution containing ethanol, but not in an aqueous alkaline solution containing other alcohols, for example, methanol or isopropanol. It was also found that the viscoelasticity of the formed hyaluronic acid gel varies depending on the reaction time. In other words, it was found that hyaluronic acid hydrogel may be formed when the aqueous alkaline solution contains especially ethanol among organic solvents. It was also found that the reaction time may be appropriately varied to form hyaluronic acid gel having a desired viscoelasticity.

The cross-linking reaction may be performed in the presence of ethanol at a temperature range higher than room temperature for rapid cross-linking reaction. This rapid cross-linking reaction may induce light cross-linking. The temperature range higher than room temperature may be from about 40 to about 60□.

The primary cross-linked product may be a cross-linked hyaluronic acid in hydrogel form. The secondary cross-linked product obtained through further cross-linking of the primary cross-linked product may be a cross-linked hyaluronic acid in particle form.

According to an experimental result, it was found that a combination of cross-linked hyaluronic acids having a desired viscoelasticity may be obtained by combination of the primary cross-linked product and the secondary cross-linked product.

Another aspect of the present disclosure provides a combination of cross-linked hyaluronic acids including a low-viscoelasticity cross-linked hyaluronic acid having an elasticity of 50 to 200 Pa and a viscosity of 20 to about 100 Pa, and a high-viscoelasticity cross-linked hyaluronic acids having an elasticity of 400 to 800 Pa and a viscosity of 40 to 100 Pa.

The low-viscoelasticity cross-linked hyaluronic acid and the high-viscoelasticity cross-linked hyaluronic acid are not limited to cross-linked hyaluronic acids prepared using a specific cross-linking method. In some embodiments, the low-viscoelasticity cross-linked hyaluronic acid and the high-viscoelasticity cross-linked hyaluronic acid may be the primary cross-linked product of hyaluronic acids and the secondary cross-linked product of hyaluronic acids, respectively, prepared using the above-described methods of preparing cross-linked hyaluronic acids.

A ratio of combination of the low-viscoelasticity cross-linked hyaluronic acid and the high-viscoelasticity cross-linked hyaluronic acid may be adjusted depending on a desired viscoelasticity of the combination of cross-linked hyaluronic acids.

Another aspect of the present disclosure provides a combination of cross-linked hyaluronic acids including a primary cross-linked product of hyaluronic acids having an elasticity of about 50 to about 200 Pa and a viscosity of about 20 to about 100 Pa, and a secondary cross-linked product of hyaluronic acids having an elasticity of about 400 to about 800 Pa and a viscosity of about 40 to about 100 Pa.

A ratio of combination of the primary cross-linked product and the secondary cross-linked product may be adjusted depending on a desired viscoelasticity of the combination of cross-linked hyaluronic acids.

Another aspect of the present disclosure provides a biocompatible material including a combination of cross-linked hyaluronic acids according to any of the above-described embodiments.

The biocompatible material may be a biocompatible material using hyaluronic acids, for example, selected from the group consisting of arthritis treatment implants, wrinkle fillers, cosmetic fillers, and drug carriers. The biocompatible material may have a target viscoelasticity that may vary depending on its use. A ratio of combination of the low-viscoelasticity cross-linked hyaluronic acid and the high-viscoelasticity cross-linked hyaluronic acid in the combination of cross-linked hyaluronic acids, or a ratio of combination of the primary cross-linked product of hyaluronic acids and the secondary cross-linked product of hyaluronic acids in the combination of cross-linked hyaluronic acids may be adjusted depending on a target viscoelasticity of the combination of cross-linked hyaluronic acids.

In some embodiments, the combination of cross-linked hyaluronic acids may be a combination of cross-linked hyaluronic acids having an elasticity of about 100 to about 150 Pa and a viscosity of about 20 to about 60 Pa, which may result in a viscoelasticity appropriate for use as a synovial fluid supplement in the human body. It is known that a viscoelasticity similar to that of human synovial fluid may be obtained at an elasticity of about 100 to about 150 Pa and a viscosity of about 20 to about 60 Pa (Balazs, E. A., "The physical properties of synovial fluid and the special role of hyaluronic acid," *Disorders of the Knee* 2 (1974): 61-74). To obtain a combination of cross-linked hyaluronic acids having such a level of viscoelasticity, the ratio of combination of the low-viscoelasticity cross-linked hyaluronic acid and the high-viscoelasticity cross-linked hyaluronic acid, or the ratio of combination of the primary cross-linked product and the secondary cross-linked product may be varied according to the molecular weight of the hyaluronic acids.

In an experiment, a high-molecular weight (about 2.5 MDa) hyaluronic acid and a low-molecular weight (about 0.9 MDa) hyaluronic acid were each subjected to a cross-linking reaction to obtain primary cross-linked products. The resulting primary cross-linked products were each subjected to a further cross-linking reaction to obtain a secondary cross-linked product. The primary cross-linked product and the secondary cross-linked product were combined in different ratios to prepare combinations of cross-linked hyaluronic acids, followed by a viscoelasticity measurement. As a result, the primary cross-linked products were found to have a different viscoelasticity depending on whether a high-molecular weight hyaluronic acid or a low-molecular weight hyaluronic acid was used as a start material. Furthermore, the secondary cross-linked products were found to have a significantly increased viscoelasticity, compared to that of their primary cross-linked product, irrespective of the molecular weight of the start material. The combination of cross-linked hyaluronic acids also each had a different viscoelasticity depending on the ratio of combination of the primary cross-linked product and the secondary cross-linked product (refer to Experimental Example 2).

To obtain a combination of cross-linked hyaluronic acids having a desired viscoelasticity, the ratio of combination of the primary cross-linked product and the secondary cross-linked product may vary depending on the molecular weight of hyaluronic acid source used as the start material. A combination ratio of about 9:1 by weight of the primary cross-linked product and the secondary cross-linked product thereof for the case of a high-molecular weight (about 2.5 MDa) hyaluronic acid source being used as the start material, or a combination ratio of 8:2 by weight of the primary cross-linked product and the secondary cross-linked product thereof for the case of a low-molecular weight (about 0.9 MDa) hyaluronic acid source being used as the start material may obtain a combination of cross-linked hyaluronic acids having a viscoelasticity range (at an elasticity of about 100 to about 150 Pa and a viscosity of about 20 to 60 Pa) appropriate for use as arthritis treatment implants (refer to Experimental Example 2).

In some embodiments, the combination of cross-linked hyaluronic acids may include the primary cross-linked product of hyaluronic acids having an elasticity of 50 to 200 Pa and a viscosity of 20 to 100 Pa and the secondary cross-linked product of hyaluronic acids having an elasticity of 400 to 800 Pa and a viscosity of 40 to 100 Pa in a weight ratio of about 8:2 to about 9:1.

In some embodiments, the combination of cross-linked hyaluronic acids may be in the form of particles, obtained by particlization, having an average particle size of about 500 to about 750 μm. The particlization may be performed by a general pulverization process after combination of the primary cross-linked product and the secondary cross-linked product.

FIG. 1 is a flowchart illustrating a method of preparing a combination of cross-linked hyaluronic acids, according to an embodiment of the present disclosure. This preparation method now will be described below.

Referring to FIG. 1, step (a) is preparing a primary cross-linked product of hyaluronic acids in hydrogel form. For example, sodium hyaluronate (also abbreviated to "HA") used in step (a) may be a product prepared by fermentation with a *Streptococcus* spp. microorganism (available from Hanmi Pharm Co., Ltd.). In particular, step (a1) is mixing a sodium hyaluronate-containing buffer with an ethanol-containing aqueous sodium hydroxide solution. A viscoelasticity of a resulting hyaluronic acid hydrogel may vary depending on a mixing ratio of ethanol and sodium hydroxide in step (a1). In the presence of about 5 to about 13% w/w of ethanol in an about 0.7 to about 1.3% w/w aqueous sodium hydroxide solution, sodium hyaluronate may be stably mixed with the ethanol, not extracted thereby, so that a cross-linking reaction may take place. Step (a2) is mixing sodium hyaluronate with a cross-linking agent. The amount of the cross-linking agent may be about 10 μl to about 100 μl per unit gram of sodium hyaluronate. When the amount of the cross-linking agent is less than this range, a cross-linked hyaluronic acid having a desired viscoelasticity may not be obtained. Step (a3) is a process of cross-linking reaction of sodium hyaluronate with a cross-linking agent in the ethanol-containing aqueous alkaline solution. In this step, rapid cross-linking reaction may be performed due to a reaction temperature higher than room temperature and the presence of ethanol in a reactant, so that a light cross-linking may be induced. This reaction step may be performed in an about 40 to about 60☐ oven for about 4 to about 6 hours. The resulting cross-linked hyaluronic acids in hydrogel form may be subjected to dialysis in a buffer (step (a4)), followed by a neutralization reaction with distilled water (step (a5)) and then precipitation of hyaluronic acid as hydrogel may be induced with about 95% ethanol (step (a6)) thereby obtaining a cross-linked hyaluronic acid in powder form.

Step (b) is preparing a secondary cross-linked product of hyaluronic acids in the form of particles through further cross-linking of the primary cross-linked product of hyaluronic acids obtained in step (a). Step (b1) is adding the cross-linked sodium hyaluronate (HA) obtained in step (a6), to an about 0.7 to about 1.3% w/w aqueous sodium hydroxide solution and mixing them together. Step (b2) is adding a cross-linking agent to the resulting mixture from step (b1) and mixing together. In this step, about 10 to about 100 μl of the cross-linking agent may be added per one gram of the cross-linked HA obtained in step (a). Step (b3) is a cross-linking reaction process of HA with the cross-linking agent. This reaction may be performed in an about 40 to about 60☐ oven for about 8 to 10 hours. This cross-linking reaction in step (b3) may be performed for a time longer than step (a3) to induce generation of cross-linked hyaluronic acids in the form of particles. The obtained cross-linked hyaluronic acids in the form of particles may be subjected to dialysis in a buffer (step (b4)), followed by a neutralization reaction with distilled water (step (b5)) and then precipitation of hyaluronic acid as particles may be induced with about 95% ethanol (step (b6)) thereby obtaining cross-linked hyaluronic acids in powder form.

Step (c) is mixing the primary cross-linked product of sodium hyaluronate in hydrogel form obtained in step (a) with the secondary cross-linked product of sodium hyaluronate in particle form obtained in step (b) in a variety of ratios, and preparing a final product via pulverization, filling, and sterilization. Step (c1) is mixing the primary cross-linked product of sodium hyaluronate in hydrogel form and the secondary cross-linked product of sodium hyaluronate in particle form in a ratio of about 9:1 to about 8:2 and dissolving the mixture in a buffer to prepare a combination of cross-linked hyaluronic acids. Step (c2) is pulverizing the combination of cross-linked hyaluronic acids into particles having a particle size of about 500 to about 750 μm, followed by filling a syringe with the combination of cross-linked hyaluronic acids (step (c3)) and sterilizing the combination of cross-linked hyaluronic acids-filled syringe (step (c4)) thereby obtaining a final combination of cross-linked hyaluronic acids having a target viscoelasticity.

In some embodiments, the biocompatible material may be a synovial fluid supplement including a combination of the cross-linked hyaluronic acid having an elasticity of 50 to 200 Pa and a viscosity of 20 to 100 Pa and the cross-linked hyaluronic acid having an elasticity of 400 to 800 Pa and a viscosity of 40 to 100 Pa, the combination in particle form having an average particle size of about 500 to about 750 μm and having an elasticity of 100 to 150 Pa and a viscosity of 20 to 60 Pa. In some embodiments, the biocompatible material may be a synovial fluid supplement including a combination of the primary cross-linked product of hyaluronic acids having an elasticity of 50 to 200 Pa and a viscosity of 20 to 100 Pa and the secondary cross-linked product of hyaluronic acids having an elasticity of 400 to 800 Pa and a viscosity of 40 to 100 Pa, the combination in particle form having an average particle size of about 500 to about 750 μm and an elasticity of 100 to 150 Pa and a viscosity of 20 to 60 Pa.

The synovial fluid supplement may have a viscoelasticity similar to that of the human's real synovial fluid, and may be effectively used as a synovial fluid supplement. The synovial fluid supplement may include both the primary cross-linked product in hydrogel form and the secondary cross-linked product in particle form to thus provide lubricating and separating functions for joints, and may serve a very similar function like the human synovial fluid. Due to the inclusion of both the primary cross-linked product in hydrogel form and the secondary cross-linked product in particle form, the biocompatible material may be structurally stable, not easily decomposable in the human body, and have an effect as a synovial fluid supplement lasting for about 6 months or longer with one injection.

Another aspect of the present disclosure provides a method of preparing a combination of cross-linked hyaluronic acids according to any of the above-described embodiments, the method including combining the cross-linked hyaluronic acid having an elasticity of about 50 to about 200 Pa and a viscosity of about 20 to about 100 Pa and the cross-linked hyaluronic acid having an elasticity of about 400 to about 800 Pa and a viscosity of about 40 to about 100 Pa, wherein the combining ratio is adjusted to meet a target viscoelasticity of the combination of cross-linked hyaluronic acids to be prepared.

According to the method, a combination of cross-linked hyaluronic acid having a desired viscoelasticity may be obtained by adjustment of the combining ratio of the cross-linked hyaluronic acids having an elasticity of about 50 to about 200 Pa and a viscosity of about 20 to about 100 Pa and the cross-linked hyaluronic acid having an elasticity of about 400 to about 800 Pa and a viscosity of about 40 to about 100 Pa. In some embodiments, by combining the cross-linked hyaluronic acid having an elasticity of about 50 to about 200 Pa and a viscosity of about 20 to about 100 Pa and the cross-linked hyaluronic acid having an elasticity of about 400 to about 800 Pa and a viscosity of about 40 to about 100 Pa in a weight ratio of about 9:1 to about 8:2, a combination of cross-linked hyaluronic acids having an elasticity of 100 to 150 Pa and a viscosity of 20 to 60 Pa, which may lead to a similar viscoelasticity as the human synovial fluid, may be obtained. To prepare a combination of cross-linked hyaluronic acids having a desired viscoelasticity, the combining ratio of the primary cross-linked product of hyaluronic acids and the secondary cross-linked product of hyaluronic acids may be varied. Even when preparing a combination of cross-linked hyaluronic acids having the same viscoelasticity, the combining ratio of the primary cross-linked product of hyaluronic acids and the secondary cross-linked product of hyaluronic acids may also be varied depending on the molecular weight of hyaluronic acid source and the preparation conditions of the primary cross-linked product and the secondary cross-linked product (reaction temperature, reaction time, and the like).

One or more embodiments of the present disclosure will now be described in detail with reference to the following examples. However, these examples are only for illustrative purposes and are not intended to limit the scope of the one or more embodiments of the present disclosure.

Preparation Example 1: Preparation of Cross-Linked HA in Organic Solvent-Free Aqueous Alkaline Solution After 10 g of sodium hyaluronate was mixed with a 1% w/w NaOH aqueous solution, 50 μl of BDDE with respect to 1 g of sodium hyaluronate was added thereto and reacted at about 40° C. for about 3, 12, or 24 hours.

Preparation Example 2: Preparation of Cross-Linked HA in Ethanol-Containing Aqueous Alkaline Solution (1)

After 10 g of sodium hyaluronate was mixed with a 1% w/w NaOH aqueous solution containing 10% w/w of ethanol, 50 μl of BDDE with respect to 1 g of sodium hyaluronate was added thereto and reacted at about 40° C. for about 3, 5, 12, or 24 hours.

Preparation Example 3: Preparation of Cross-Linked HA in Ethanol-Containing Aqueous Alkaline Solution (2)

After 10 g of sodium hyaluronate was mixed with a 1% w/w NaOH aqueous solution containing 10% w/w of ethanol, 50 µl of EGDGE with respect to 1 g of sodium hyaluronate was added thereto and reacted at about 40° C. for about 24 hours.

Preparation Example 4: Preparation of Cross-Linked HA in Ethanol-Containing Aqueous Alkaline Solution (3)

After 10 g of sodium hyaluronate was mixed with a 1% w/w NaOH aqueous solution containing 10% w/w of ethanol, 50 µl of 1,6-hexanediol diglycidyl ether with respect to 1 g of sodium hyaluronate was added thereto and reacted at about 40° C. for about 24 hours.

Preparation Example 5: Preparation of Cross-Linked HA in Methanol-Containing Aqueous Alkaline Solution After 10 g of sodium hyaluronate was mixed with a 1% w/w NaOH aqueous solution containing 10% w/w of methanol, 50 µl of BDDE with respect to 1 g of sodium hyaluronate was added thereto and reacted at about 40° C. for about 3, 12, or 24 hours.

Preparation Example 6: Preparation of Cross-Linked HA in Isopropanol-Containing Aqueous Alkaline Solution After 10 g of sodium hyaluronate was mixed with a 1% w/w NaOH aqueous solution containing 10% w/w of isopropanol, 50 µl of BDDE with respect to 1 g of sodium hyaluronate was added thereto and reacted at about 40° C. for about 3, 12, or 24 hours.

Experimental Example 1: Gelation Observation and Viscoelasticity Measurement of Cross-Linked HA Prepared in Preparation Examples 1 to 6

It was identified whether gelation occurred or not in the cross-linked HA of Preparation Examples 1 to 6 by naked-eye observation, and viscoelasticity measurements were performed. The viscoelasticity measurement was performed with a rotational rheometer (Kinexus Pro Rheometer, available from Malvern, Worchestershire, UK). Dynamic viscoelasticity was measured with a cone having a diameter of 20 mm at a cone-plate distance (GAP) of about 0.5 mm. The temperature was maintained constant at about 25° C. until the end of the analysis. The viscoelasticity measurement was performed with a control program in an oscillation mode at a frequency of about 0.1 to 5 Hz to measure a storage modulus G' and a loss modulus G". The storage modulus G' means energy stored in a sample (elasticity behavior), and the loss modulus G" means lost energy (viscosity behavior). The results are shown in Tables 1 and 2.

TABLE 1

| | Reaction condition | | Reaction result |
|---|---|---|---|
| | Organic solvent | Reaction time at 40° C. | Gelation |
| Preparation Example 1 | None | 3 hr | No gelation occurred |
| | | 12 hr | Gelation occurred |
| | | 24 hr | Gelation occurred |
| Preparation Example 2 | ethanol | 3 hr | No gelation occurred |
| | | 5 hr | Gelation occurred |
| | | 12 hr | Gelation occurred |
| | | 24 hr | Gelation occurred |
| Preparation Example 3 | ethanol | 24 hr | Gelation occurred |
| Preparation Example 4 | ethanol | 24 hr | Gelation occurred |
| Preparation Example 5 | methanol | 3 hr | No gelation occurred |
| | | 12 hr | No gelation occurred |
| | | 24 hr | No gelation occurred |
| Preparation Example 6 | isopropanol | 3 hr | No gelation occurred |
| | | 12 hr | No gelation occurred |
| | | 24 hr | No gelation occurred |

TABLE 2

| | Reaction condition | | Reaction result | | |
|---|---|---|---|---|---|
| | Organic solvent | Reaction time at 40° C. | Gelation | Viscoelasticity | |
| | | | | G' | G" |
| Preparation Example 1 | None | 3 hr | No gelation | — | — |
| | | 12 hr | Gelation occurred | 1789.7 | 300.8 |
| | | 24 hr | Gelation occurred | 2377.7 | 369.8 |
| Preparation Example 2 | ethanol | 3 hr | No gelation | — | — |
| | | 5 hr | Gelation occurred | 78.8 | 29.6 |
| | | 12 hr | Gelation occurred | 379.2 | 63.3 |
| | | 24 hr | Gelation occurred | 1908.3 | 356.2 |

Referring to the results of Tables 1 and 2, it was found that gelation occurred in the cross-linked hyaluronic acids of Preparation Example 1 using the organic solvent-free aqueous alkaline solution and in Preparation Examples 2 to 4 using the ethanol-containing aqueous alkaline solution. However, the cross-linking reaction could not be continued after the cross-linking reaction for 24 hours, due to browning of hyaluronic acids.

The cross-linked hyaluronic acids of Preparation Example 2 using the ethanol-containing aqueous alkaline solution were found to have a significantly low viscoelasticity, compared to the cross-linked hyaluronic acids of Preparation Example 1 using the organic solvent-free aqueous alkaline solution. This indicates that adding ethanol to an aqueous alkaline solution for a cross-linking reaction may suppress the cross-linking reaction, and consequentially result in cross-linked hyaluronic acids having a reduced viscoelasticity.

In Preparation Examples 5 and 6 using an aqueous alkaline solution containing a lower alcohol other than ethanol, even after the cross-linking reaction occurred for a long time, the cross-linked hyaluronic acids in hydrogel form were not generated.

Example 1: Preparation of Primary Cross-Linked Product of Hyaluronic Acids in Hydrogel Form The preparation processes of Examples 1 to 3 were separately performed using each of a high-molecular weight sodium hyaluronate (having a molecular weight of 2.5 Mda) and a low-molecular weight sodium hyaluronate (having a molecular weight of 0.9 Mda). The high-molecular weight sodium hyaluronate (having a molecular weight of 2.5 Mda) and the low-molecular weight sodium hyaluronate (having a molecular weight of 0.9 Mda) both produced by fermentation with a *Streptococcus* spp. microorganism (*Streptococcus zooepidemicus*) were obtained from Hanmi Pharm Co., Ltd.

After sodium hyaluronate was added to a mixed solvent containing 1% w/w of a sodium hydroxide aqueous solution and 10% w/w of ethanol and completely dissolved, 50 μl of BDDE with respect to 1 g of sodium hyaluronate was added thereto and mixed together. After the mixing, a cross-linking reaction was performed at a reaction temperature of about 40° C. for about 5 hours. After termination of the reaction, the resulting primary cross-linked product of hyaluronic acids in hydrogel form were subjected to dialysis in a phosphate buffered saline (PBS) buffer, followed by washing with distilled water to remove BDDE. The resulting neutralized hydrogel was subjected to extraction with a 95% ethanol aqueous solution thereby yielding a primary cross-linked product of hyaluronic acids in powder form.

Example 2: Preparation of Secondary Cross-Linked Product of Hyaluronic Acids in Particle Form The primary cross-linked product of hyaluronic acids obtained in Example 1 was subjected to a secondary cross-linking reaction. The primary cross-linked product of hyaluronic acids in powder form obtained in Example 1 was mixed with a 1% w/w sodium hydroxide aqueous solution in a weight ratio of about 1:5 and then completely dissolved. 50 μl of BDDE with respect to 1 g of the primary cross-linked product was added to the resulting reaction mixture and then mixed together. After the mixing, a cross-linking reaction was performed at a reaction temperature of about 40☐ for about 8 hours. After termination of the reaction, the resulting secondary cross-linked product of hyaluronic acids in particle form was subjected to dialysis in a PBS buffer for about 12 to 24 hours, followed by washing with distilled water to remove BDDE. The resulting neutralized hyaluronic acids in particle form were subjected to extraction with a 95% ethanol aqueous solution to thereby yield a secondary cross-linked product of hyaluronic acids in powder form.

Example 3: Preparation of a Combination of Cross-Linked Hyaluronic Acids

The primary cross-linked product of hyaluronic acids in hydrogel form obtained in Example 1 and the secondary cross-linked product of hyaluronic acids in particle form obtained in Example 2 were mixed together in a weight ratio of about 9:1 or about 8:2 in a PBS buffer to prepare a 2% w/w of mixed solution. The mixed solution was pulverized by passing the mixed solution through a 500 μm-mesh sieve with physical force. The pulverized mixture was filled into a syringe, followed by sterilization at about 121° C. for about 20 minutes.

Experimental Example 2: Viscoelasticity Measurement of Combinations of Cross-Linked Hyaluronic Acids The primary cross-linked product of hyaluronic acids in hydrogel form obtained in Example 1 and the secondary cross-linked product of hyaluronic acids in particle form obtained in Example 2 were mixed together in a weight ratio of about 10:0, 9:1, 8:2, and 0:10 in a PBS buffer to prepare 2% w/w of mixed solutions. The mixed solutions were each pulverized by passing them through a 500 μm-mesh sieve with physical force. The viscoelasticity of each of the mixed solutions was measured using a rotational rheometer (Kinexus Pro Rheometer, available from Malvern, Worchestershire, UK). The results are shown in Table 3.

TABLE 3

| Experiment condition | | Result | |
|---|---|---|---|
| Hyaluronic acids | Mixed ratio by weight [Primary to Secondary] | Elasticity (G') [Pa/2.5 Hz] | Viscosity (G") [Pa/2.5 Hz] |
| 2.5 MDa hyaluronic acids | 10:0 | 78.8 | 29.6 |
| | 9:1 | 114.40 | 45.19 |
| | 8:2 | 162.30 | 53.76 |
| | 0:10 | 712.70 | 88.50 |
| 0.9 MDa hyaluronic acids | 10:0 | 55.35 | 28.50 |
| | 9:1 | 70.38 | 34.94 |
| | 8:2 | 106.10 | 45.71 |
| | 0:10 | 435.50 | 48.43 |

Referring to the results of Table 3, the combinations of cross-linked hyaluronic acids had a different viscoelasticity depending on a mixed ratio of the primary cross-linked product to the secondary cross-linked product.

The combination of cross-linked hyaluronic acids obtained with the primary cross-linked product and secondary cross-linked product from the high-molecular weight hyaluronic acid in a mixed ratio of about 9:1 by weight had an elasticity of about 114.40 Pa and a viscosity of about 45.19 Pa. The combination of cross-linked hyaluronic acids obtained with the primary cross-linked product and secondary cross-linked product from the low-molecular weight hyaluronic acids in a mixed ratio of about 8:2 by weight had an elasticity of 106.1 Pa and a viscosity of 45.71 Pa. Accordingly, these two combinations of cross-linked hyaluronic acids were found to have a similar viscoelasticity to the human synovial fluid.

The viscoelasticities of the cross-linked hyaluronic acid prepared under the same conditions varied depending on the molecular weight of the starting hyaluronic acid source. Even prepared under the same cross-linking conditions, the cross-linked hyaluronic acid from the starting high-molecular weight hyaluronic acid source had a higher viscoelasticity than those from the starting low-molecular weight hyaluronic acid source. Therefore, to prepare a combination of cross-linked hyaluronic acids having a desired viscoelasticity, the combination ratio of the primary cross-linked product and the secondary cross-linked product may vary depending on the molecular weight of a starting hyaluronic acid source.

Experimental Example 3: Particle Size Analysis of a Combination of Cross-Linked Hyaluronic Acids The particle size of the combination of cross-linked hyaluronic acids obtained with the primary cross-linked product and secondary cross-linked product of the high-molecular weight hyaluronic acids in a mixed ratio of about 9:1 by weight, found to have a similar viscoelasticity to the human synovial fluid in Experimental Example 2, was analyzed using a particle size analyzer (available from Microtrac, Montgomeryville, Pa.).

Figure 2:
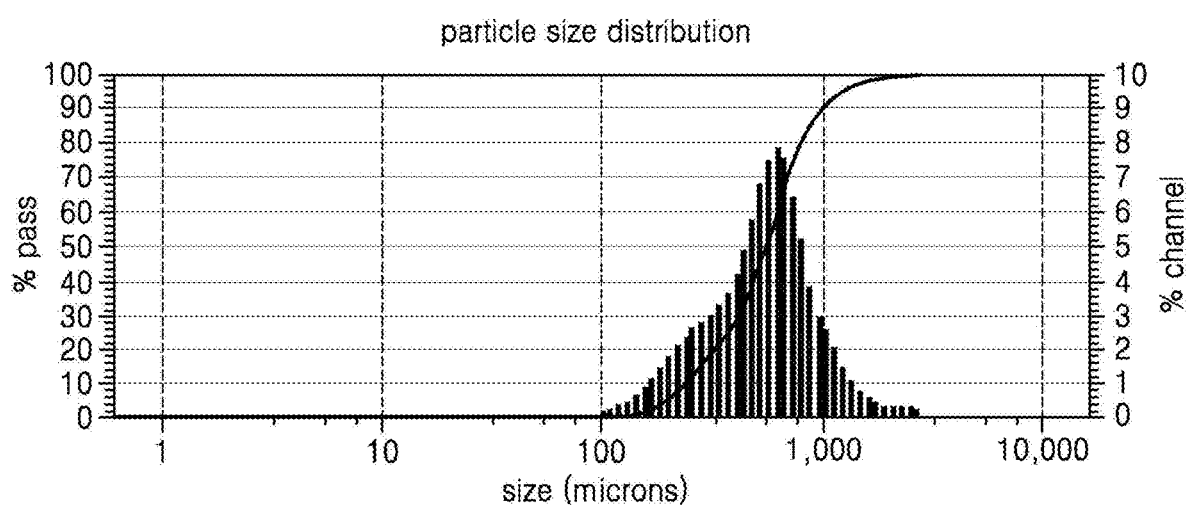
FIG. 2 is a graph of particle size distribution as a result of measuring particle sizes of a combination of cross-linked hyaluronic acids prepared with the primary cross-linked product and secondary cross-linked product of high-molecular weight (about 2.5 MDa) hyaluronic acids in a mixed ratio of about 9:1 by weight, according to an embodiment of the present disclosure.

The resulting particle size distribution of the combination of cross-linked hyaluronic acids is shown in FIG. 2.

Referring to FIG. 2, the combination of cross-linked hyaluronic acids was found to have an average particle size of about 606 μm ($D_{10}$: 235.8 μm, $D_{50}$: 553.5 μm, and $D_{90}$: 1009 μm).

Experimental Example 4: Cytotoxicity Assay

Cytotoxicity of the combination of cross-linked hyaluronic acids obtained with the primary cross-linked product and secondary cross-linked product from the high-molecular weight hyaluronic acids in a mixed ratio of about 9:1 by weight, found to have a similar viscoelasticity to the human synovial fluid in Experimental Example 2, was evaluated by the MTT (3-(4,5-dimethyl-2-thiazolyl)-2,5-diphenyltetrazolium) assay.

According to the MTT assay, toxicity of an elution from the combination of cross-linked hyaluronic acids for about 72 hours was evaluated, together with toxicity of elutions from Teflon as a positive control group and Latex as a negative control group. The results of cell survival ratios obtained from the MTT assay ware shown in FIG. 3.

Figure 3:
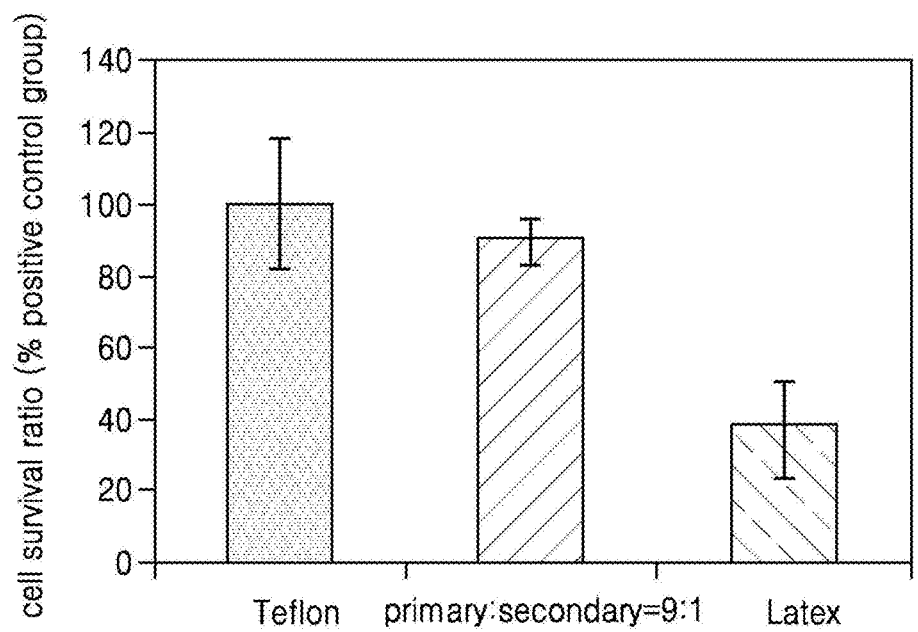
FIG. 3 is a graph of cell survival ratio illustrating the results of the MTT (3-(4,5-dimethyl-2-thiazolyl)-2,5-diphenyltetrazolium) assay on the combination of cross-linked hyaluronic acids prepared with the primary cross-linked product and secondary cross-linked product of high-molecular weight hyaluronic acids in a mixed ratio of about 9:1 by weight, according to an embodiment of the present disclosure, and positive (Teflon) and negative (Latex) control groups.

Referring to the results of FIG. 3, the cell survival ratios of Teflon and Latex were 100% and 37%, respectively. The combination of cross-linked hyaluronic acids had a cell survival ratio of about 89.93%, which is above 80%, the lower limit of cytotoxicity. Therefore, the combination of cross-linked hyaluronic acids as an embodiment of the present disclosure was found to have high biocompatibility.

While this invention has been particularly shown and described with reference to preferred embodiments thereof, it will be understood by those skilled in the art that various changes in form and details may be made therein without departing from the spirit and scope of the invention as defined by the appended claims. The disclosed embodiments should be considered in descriptive sense only and not for purposes of limitation. Therefore, the scope of the invention is defined not by the detailed description of the invention but by the appended claims, and all differences within the scope will be construed as being included in the present invention.

The invention claimed is:

1. A method of preparing a combination of cross-linked hyaluronic acids having an elasticity of about 100 to about 150 Pa at 2.5 Hz and a viscosity of about 20 to about 60 Pa at 2.5 Hz comprising:
combining (a) a cross-linked hyaluronic acid having an elasticity of about 50 to about 200 Pa at 2.5 Hz and a viscosity of about 20 to about 100 Pa at 2.5 Hz with (b) a cross-linked hyaluronic acid having an elasticity of about 400 to about 800 Pa at 2.5 Hz and a viscosity of about 40 to about 100 Pa at 2.5 Hz;
wherein the (a) cross-linked hyaluronic acid is prepared by a method comprising cross-linking hyaluronic acid with an epoxy-based cross-linking agent having at least two epoxy functional groups in an ethanol-containing aqueous alkaline solution;
wherein the (b) cross-linked hyaluronic acid is prepared by a method comprising cross-linking the cross-linked hyaluronic acid having an elasticity of about 50 to about 200 Pa at 2.5 Hz and a viscosity of about 20 to about 100 Pa at 2.5 Hz with an epoxy-based cross-linking agent having at least two epoxy functional groups in an aqueous alkaline solution;
wherein the combining ratio of the (a) cross-linked hyaluronic acid to the (b) cross-linked hyaluronic acid is about 9:1 to about 8:2 by weight; and
wherein the hyaluronic acid has a molecular weight of about 100,000 to about 6,000,000.

2. The method of claim 1, wherein the hyaluronic acid is obtained by fermentation with a microorganism.

3. The method of claim 1, wherein the hyaluronic acid includes hyaluronic acid, a salt of hyaluronic acid, or a mixture thereof.

4. The method of claim 3, wherein the salt of hyaluronic acid is selected from the group consisting of sodium hyaluronate, potassium hyaluronate, magnesium hyaluronate, zinc hyaluronate, cobalt hyaluronate, tetrabutylammonium hyaluronate, and a combination thereof.

5. The method of claim 1, wherein the epoxy-based cross-linking agent having at least two epoxy functional groups is selected from the group consisting of 1,4-butanediol diglycidyl ether (BDDE), ethylene glycol diglycidyl ether (EGDGE), 1,6-hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, trimethylpropane polyglycidyl ether, 1,2-(bis(2,3-epoxypropoxy)ethylene, pentaerythritol polyglycidyl ether, sorbitol polyglycidyl ether, and a combination thereof.

6. The method of claim 1, wherein the ethanol-containing aqueous alkaline solution contains about 5 to about 13% w/w of ethanol.

7. The method of claim 1, wherein the ethanol-containing aqueous alkaline solution is an aqueous sodium hydroxide solution of about 0.7 to 1.3% w/w containing about 5 to about 13% w/w of ethanol.

* * * * *